United States Patent [19]

Albarda et al.

[11] Patent Number: 4,763,509
[45] Date of Patent: Aug. 16, 1988

[54] DEVICE FOR DETERMINING THE CONCENTRATION OF SUBSTANCES HAVING PARAMAGNETIC PROPERTIES

[75] Inventors: Scato Albarda, Gross Schenkenberg; Alfred Eder, Wultertshausen, both of Fed. Rep. of Germany

[73] Assignee: Drägerwerk AG, Fed. Rep. of Germany

[21] Appl. No.: 943,541

[22] Filed: Dec. 17, 1986

[30] Foreign Application Priority Data

Dec. 19, 1985 [DE] Fed. Rep. of Germany ....... 3544966

[51] Int. Cl.$^4$ ............................................. G01R 33/12
[52] U.S. Cl. ...................................... 73/27 A; 324/204
[58] Field of Search ........................ 73/23, 27 R, 27 A; 324/204

[56] References Cited

U.S. PATENT DOCUMENTS

| | | | |
|---|---|---|---|
| 2,689,332 | 9/1954 | Greene | 73/27 A |
| 3,076,929 | 2/1963 | Gillerman | 324/204 |
| 3,714,557 | 1/1973 | Gast | 73/27 A |
| 3,742,344 | 6/1973 | Hummel | 73/27 A |

FOREIGN PATENT DOCUMENTS 1924228 11/1970 Fed. Rep. of Germany .

Primary Examiner—Tom Noland
Assistant Examiner—Hezron E. Williams
Attorney, Agent, or Firm—McGlew and Tuttle

[57] ABSTRACT

A device for the determination of the concentration of substances with paramagnetic properties, particularly oxygen, in substance mixtures comprises a cell assembly and devices to produce a magnetic field as well as to measure changes in the magnetic induction. Great mechanical accuracy and stability in the measuring of a change in the magnetic induction uninfluenced by external disturbing fields or by mechanical changes due to external temperature fluctuations or vibrations with a coil assembly for producing a magnetic field and for measuring the induction signal comprising self-contained coil carriers, which, surrounding a cell assembly and are arranged respectively at a distance from the axis of rotation of the cell assembly.

6 Claims, 1 Drawing Sheet

DEVICE FOR DETERMINING THE CONCENTRATION OF SUBSTANCES HAVING PARAMAGNETIC PROPERTIES

FIELD AND BACKGROUND OF THE INVENTION

This invention relates in general to gas detection devices and in particular to a new and useful device for determining the concentration of substances with paramagnetic properies, particularly oxygen.

The invention particularly concerns a device for the determination of the concentration of substances with paramagnetic properties, particularly oxygen, in substance mixtures consisting of a revolving, subdivided cell assembly, in which a first series of cells is filled with gas having variable oxygen contents and a second series of cells contains a control gas with a constant oxygen content, and an assembly of coils in which the magnetic induction produced by the parmagnetic substance is converted into an electrical signal.

A similar device is known from German OS No. 19 24 228, in which is described a first magnet system, consisting of permanent magnet, pole shows and magnetic air gap, and a second, identical magnet system which extends over a revolving chamber system. The chamber system is constructed with a centrifugal force fan wheel of circular disc shape and open chambers, through which the gas to be measured flows alternating and with closed chambers with a control gas being passed between the pole shoes of both permanent magnets. The chamber sequence is arranged to have a chamber with a control gas between the pole shoes of the first permanent magnet when a chamber with a test gas is located between the pole shoes of the second permanent magnet. The magnetic induction produced by the permanent magnets is changed into an electrical signal by measuring coils, which, at constant rpm of the measuring chamber assembly, is proportional to the partial oxygen pressure of the gas to be measured. This measuring voltage is further electrically processed and indicated on an indicator.

The known measuring device requires, however, a mechanical design of the pole shoes of the permanent magnet which guarantees a constant geometric arrangement under operating conditions. This can be obtained only at unjustifiable expense. For example, a change in the air gap between the poles of the permanent magnet by approximately $10^{-8}$ mm has an effect on the measuring signal given in the coil assembly similar to a change in the oxygen content in the test gas by approximately 1% by volume. Thus, if the oxygen concentration is to be measured with the aid of such a known assembly with an accuracy greater than 1% by volume of oxygen as is usual in practice, then the gaps between the poles of the permanent magnets must be produced with an accuracy greater than $10^{-8}$ mm and kept at this distance since changes in the gaps, e.g. due to mechanical vibrations result in disturbing microphonic effects. Such exacting demands on the mechanical processing and stability makes the applicability of the known assembly in actual practice doubtful.

The gap between the pole shoes of the magnets is no longer important when, for example, the magnet pole and coil assembly is located on only one side of the revolving cell assembly. But in this case there is the disadvantage that the magnetic field does not completely penetrate the measuring chamber and the control chamber.

It is known from U.S. Pat. No. 3,076,929 and German OS No. 31 45 542 that there are problems in arranging the mechancial chamber and control chamber firmly in a housing and surrounding both chambers with one pair of coils each. The former coil is used to produce a magnetic field and the latter coil, for the transformation of the change in its magnetic induction into an electrical signal. The coils are connected either by a transformer connection (U.S. Pat. No. 3,076,929) or by a bridge connection (German OS No. 31 45 542), and the measuring signal as produced by them are indicated in an evaluating unit.

In these known coil assemblies the test gas and the control gas serve as coil shells or jackets. The self-induction of the coil is thereby changed in proportion to the concentration of paramagnetic components in the gas mixture. This change in the induction causes an unbalance in the measuring circuit the size of which can be used to determine the concentration of paramagnetic substances.

Such a measuring device does react with sensitivity to changes in the concentration of paramagnetic substances in the test gas, but additional efforts are required to prevent variations in the expansions of the coil carriers due to variations in ambient temperatures, or at least to equalize these. A change in the geometric expansions of the coils due to temperature fluctuations is reflected in a change of their self-induction, which is on the same order of magnitude as the change in the self-induction due to the change in the concentration of paramagnetic substance in the measuring chamber.

SUMMARY OF THE INVENTION

The present invention provides a device for the determination of the concentration of substances with paramagnetic properties, particularly oxygen, in substance mixtures in such a way that the measuring of a change in the magnetic induction in a coil body can be carried out unaffected by the device producing the magnetic field and uninfluenced by temperature fluctuations or vibrations in the environment.

In accordance with the invention, the coil assembly is constructed as self-contained coil carriers, which, respectively surround the cell assembly and are located at a distance from the axis of rotation of the cell assembly.

A coil assembly according to the invention produces a magnetic field that completely penetrates the subdivided cell assembly, and mechanical irregularities in the cell assembly as well as geometric changes in the coil assembly have only an insignificant effect on the accuracy of the measuring signal. Beyond this, any screening against interfering environmental magnetic fields, which is needed for the known assembly with permanent magnets, for example, is unnecessary.

In an advantageous practical example of the invention, each of the two coil carriers has a first winding for the production of the magnetic field and a second winding for the measuring of the paramagnetic induction.

The cell assembly is divided to advantage into two halves by a separating wall, the control gas being contained in one half and the test gas flowing through the other half. Here the magnetic field penetrates the entire volume of the two chamber halves as soon as the separating wall is lined up parallel to both coil carriers. With a proper direction of current in the coil windings, the lines of magnetic force first extend in the direction toward the axis of the diameter of the cell assembly, then are turned around at its height and then extend in the direction toward the outer surfaces of the cell assembly. A penetration of the magnetic field into the respective other chamber does not occur. This results in a particularly distinct signal difference between measuring and control signal.

The measuring chamber can be constructed preferably in the form of a semi-circular disc on either side, which is attached to the separating wall. In this case, the test gas is located above and below the semicircular disc. The dimensions of the disc are of such size that a uniform dynamic balancing of the cell assembly is produced and the cell assembly forms a constant dielectric in the magnetic field.

The cell assembly comprises a sintered aluminum oxide ceramic, since this combines the important properties. This material is mechancially stable and also a good insulator, which prevents the occurrence of eddies.

Accordingly, it is an object of the invention to provide an improved device for determining the concentration of substances with paramagnetic properties and in oxygen which comprises a rotatable hollow container which has an axis of rotation and is divided by a partition into an assembly of a plurality of cells which includes means for providing a gas to be tested in at least one of the cells and the controlled gas in at least one of the other cells and including a coil assembly for producing a magnetic induction for picking up the magnetic induction produced by the substance with paramagnetic properties which surround the assembly of cells and is spaced from the axis of rotation.

A further object of the invention is to provide a method of testing gases for the presence of gases which have paramagnetic properties and which comprises directing the gas to be detected into hollow cylinder which has an inlet adjacent the axis of rotation of the cylinder and a peripheral discharge and is adjacent another chamber having a test gas which comprises producing a magnetic field around the cylinder as the cylinder is rotated, and measuring the magnetic induction produced in the substance to be tested as a determination of the gas which is present.

A further object of the invention is to provide a device for determining the concentration of a substance with magnetic properties which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
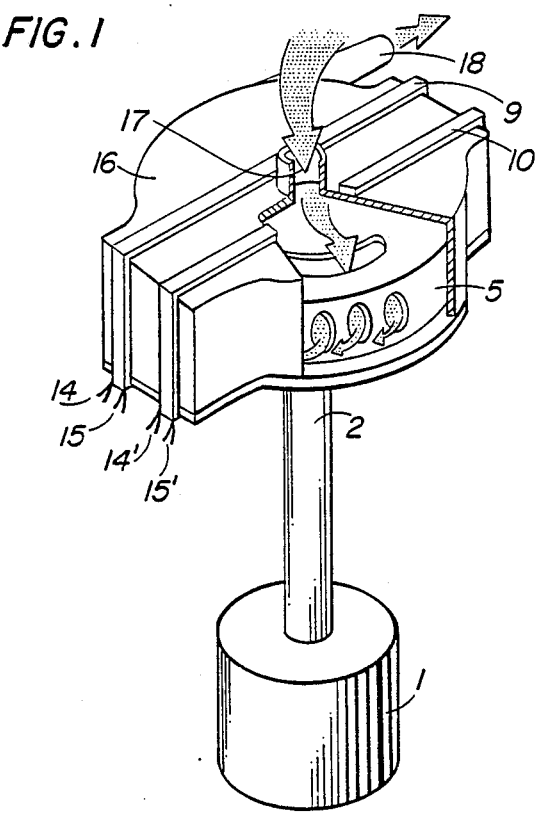
FIG. 1 is a perspective top view of a device for determining the concentration of substances with paramagnetic properties showing part of the housing removed and constructed in accordance with the invention.

Referring to the drawings in particular the invention embodied therein comprises a device for determining the concentration of substances with paramagnetic properties particularly oxygen which comprises a rotatable hollow container generally designated 30 which has an axis of rotation which is also an axis of rotation of a shaft 2 of an electric motor 1. In accordance with the invention, the container 30 has partition means in the form of a partition wall 8 which divides it into an assembly of a plurality of cells 12 and 13 which in this embodiment comprises a cell 12 provides a space for a control gas and the other cell 13 provides a cell for gas to be tested. The coil assembly 14,15 and 14' and 15' for producing a magnetic induction and for picking up the magnetic induction provided by the substance with paramagnetic properties surrounds the assembly of cells and is spaced from the axis of rotation 32.

Figure 2:
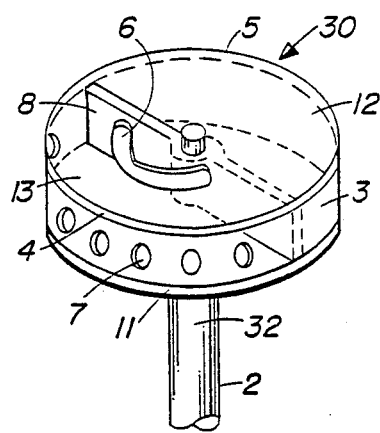
FIG. 2 is a view similar to FIG. 1 showing the cell assembly enlarged.

FIGS. 1 and 2 show a revolving cell assembly in the form of a circular hollow cylinder 5. The hollow cylinder 5 includes top and bottom circular wall elements 4 and 11, one located opposite the other, and a ring-shaped wall element 3. The cylinder 5 is separated into two chamber halves 12 and 13 by a separating wall 8. The upper chamber wall 4 has a cut-out or slot 6 over chamber half 13, which allows the test gas to enter. Side wall 3 has numerous apertures 7 in the partial area with which it surrounds chamber half 13. Chamber half 12 is closed on all sides and contains a control gas of constant composition. Hollow cylinder 5 is connected to motor 1 by a shaft 2, which is centrally attached to lower chamber wall 11. Hollow cylinder 5 is enclosed in housing 16, which contains a central top intake passage and opening 17 and a side outlet opening and passage 18 for the test gas. Coil carriers 9 and 10 are arranged around housing 16, surrounding the hollow cylinder 5. Each coil carrier 9 and 10 extends around the cylinder 5 and carries respective coil windings 14, 15 and 14', 15', which form magnetic-field-producing coil 14,14' and, a coil 15,15' that pickes up the magnetic induction signal. Coil carriers 9 and 10 are arranged parallel to each other at such a distance from the rotational axis of hollow disc 5 that they surround the respective chamber halves 12 and 13 when separating wall 8 is positioned parallel to these coil carriers 9 and 10 during the rotation of hollow disc 5. The ends of the two coil windings on each coil carrier may be connected together in a well known manner (not shown), either in the form of a bridge connection or a transformer connection, and their electrical signal can be recorded by a known evaluating unit (also not shown).

The device according to the invention functions in the following manner: Motor 1 drives hollow disc 5 with a uniform rotation in a constant direction of rotation. Due to the rotation, the hollow cylinder 5 acts as a promoter of a centrifugal force, which allows the test gas to enter the housing through intake opening 17, from where it is sucked into measuring chamber 13 through cut-out 6 and expelled through the opening 7 of side wall 3 into outlet opening 18. A high frequency magnetic alternating field in the field coils 14,14' produces a magnetic field in the test gas as well as in the control gas, which causes the magnetic moments of the paramagnetic substances to orient themselves in the direction of the outer magnetic field. The resulting magnetization is transformed into an electrical signal by coils 15,15', which is led to an evaluating unit and is evaluted by it.

Figure 3:
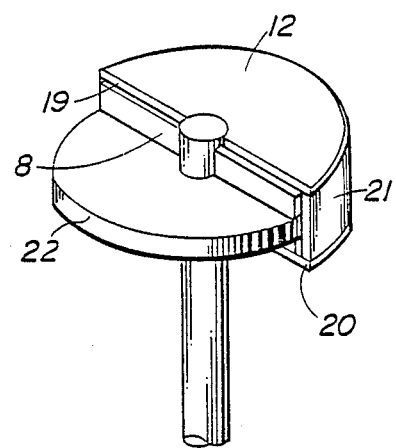
FIG. 3 is a view similar to FIG. 1 of another embodiment of the cell assembly.

FIG. 3 shows a revolving cell assembly with chamber 12, which contains the control gas, in the form of a semicircular hollow cylinder that is enclosed by an upper chamber wall 19, a lower chamber wall 20 and a side wall 21. On the other side, separating wall 8 carries at one half the height a semicircular hollow cylinder 22, the thickness of which corresponds approximately to twice the wall thickness of chamber wall 19 and 20, and which provides the cell assembly with a balanced dynamic and dielectric behavior.

When such a cell assembly is placed in housing 16, the rotary motion alternately places the control gas in chamber 12 and the test gas, which is located above and, below the cylinder 22, into the magnetic field produced by coils 14, 14' similar to FIGS. 1 and 2.

While specific embodiments of the invention have been shown and described in detail to illustrate the application of the principles of the invention, it will be understood that the invention may be embodied otherwise without departing from such principles.

What is claimed is:

1. In a device for determining the concentration of a substance with paramagnetic properties, comprising a rotatable hollow container having an axis of rotation and having a partition dividing it into an assembly of a plurality of cells, means for providing a gas to be tested in at least one of said cells and a control gas in at least one of said cells, a coil assembly for producing a magnetic induction and for picking up the magnetic induction produced by a substance with paramagnetic properties surrounding said assembly of cells and being spaced from the axis of rotation, the improvement comprising a first compartment extending around said hollow cylinder at a spaced location from the axis thereof and having a coil for producing magnetic induction, and a second compartment extending around said hollow cylinder having a coil for detecting the paramagnetic properties of the gas being tested and being spaced from the axis of rotation.

2. A device according to claim 1, wherein said device has a housing defining a chamber for said coil assembly on each side of the axis of rotation thereof, each including the first coil for producing magnetic induction and a second coil winding for producing an electrical signal corresponding to the magnetic induction.

3. A device according to claim 1, wherein said partition divides said cell assembly into two half compartments, one of said compartments comprising a measuring compartment, and the other of said compartments comprising a closed control gas compartment having a known concentration of the gas which is to be determined.

4. A device according to claim 1, wherein said container comprises a hollow cylinder, said partition dividing said cylinder into a test gas chamber and a control gas chamber, said test gas chamber including a central opening for the inflow of a test gas and a peripheral dishcarge for the test gas.

5. A device according to claim 4, including a housing surrounding said container, said container comprising a hollow cylinder having a top inlet opening over the test gas chamber said test gas chamber opening below said top inlet opening having a peripheral discharge opening.

6. A device according to claim 1, wherein said cell assembly comprises a sintered aluminum oxide ceramic.

* * * * *